United States Patent [19]
Carroll et al.

[11] Patent Number: 5,128,118
[45] Date of Patent: Jul. 7, 1992

[54] COCAINE RECEPTOR BINDING LIGANDS

[75] Inventors: Frank I. Carroll, Durham; Anita H. Lewin, Chapel Hill; Philip Abraham, Cary, all of N.C.; Michael J. Kuhar; John W. Boja, both of Baltimore, Md.

[73] Assignee: Research Triangle Institute, Research Triangle Park, N.C.

[21] Appl. No.: 564,755

[22] Filed: Aug. 9, 1990

[51] Int. Cl.$^5$ .................... A61K 49/02; C07D 451/02
[52] U.S. Cl. ..................................... 424/1.1; 546/132
[58] Field of Search ......................... 424/1.1; 546/132

[56] References Cited

PUBLICATIONS

Madras, B. K. et al, *Mol. Pharmacol*, "Cocaine Receptors . . . Tropane", 36(4), 1989, pp. 518–524, [CA 112(1):539p].

*Primary Examiner*—John S. Maples
*Attorney, Agent, or Firm*—Oblon, Spivak, McClelland, Maier & Neustadt

[57] ABSTRACT

3$\beta$-[4-iodophenyl]-tropan-2$\beta$-carboxylic acid methyl ester tartrate is a high affinity binding ligand for neurotransmitters in mammalian brains. It and its congeners may be employed for imaging and other brain scanning techniques that allow the determination of the presence of cocaine receptors, such as neurotransmitters and the like.

6 Claims, No Drawings

COCAINE RECEPTOR BINDING LIGANDS

FIELD OF THE INVENTION

This invention is directed to a binding ligand for cocaine and other neurotransmitter receptors in the brain. Specifically, a novel family of compounds, represented by 3β-[4-iodophenyl]-tropan-2β-carboxylic acid methyl ester tartrate shows high binding specificity and activity, and, in a radiolabeled form, can be used to bind to these receptors, for biochemical or imaging techniques.

BACKGROUND OF THE INVENTION

Continuing attempts to understand, diagnose, treat and prevent neural disorders rely, in part, on localization or imaging techniques, allowing researchers to determine the location, number, and size of specific neurological phenomena. Among those sites undergoing specific testing are cocaine receptors and dopamine transporter sites, as well as other neurotransmitter sites.

In order to be useful as a binding ligand for these types of imaging techniques, the compound must have a high affinity for the receptors in question. One such example is the tritiated compound [$^3$H]WIN 35,428, discussed in conjunction with the protocol for determining the relative affinity of binding ligands set forth in the presentation of Carroll et al, 19th Annual FASEB Meeting, Washington, D.C. (1990). Compounds exhibiting high affinity have previously been demonstrated to be useful as binding ligands, in in vitro and in vivo processes. Madras et al, *Molecular Pharmacology*, 36, 518–524 (1989) and Scheffel et al, *Synapse*, 4, 390–394 (1989).

In processes of this type, a radioactively labeled, or similarly labeled compound is administered or injected, depending on in vivo or in vitro processing, and allowed to bind to the sites in question. Thereafter, those sites actually bound to can be determined, by radiographic imaging techniques and the like. In one example, diagnosis of Parkinson's disease may be accomplished by administering a binding ligand having a high affinity for dopamine transporters, and subsequently subjecting the brain to SPECT scanning. The relative frequency of bound sites and imaging obtained allows an assessment of the presence or absence of Parkinson'-disease.

Many radioactively labeled ligands, such as the tritiated compound discussed above, or other tritiated or carbon-14 labeled compounds lack sufficient specific activity or affinity are subject to specimen quenching and absorption. Additionally, ideally radiolabeled binding ligands should be useful in powerful scanning and imaging techniques, such as SPECT scanning and the like. Thus, improved binding ligands exhibiting these advantages continue to be an object of those of skill in the art.

SUMMARY OF THE INVENTION

The family of compounds having the following structure:

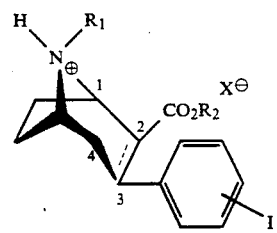

where the broken line represents an optional chemical bond and the substituents at 2 and 3 may be at any position;

the iodo substituent may be at o, m, p, or multisubstituted;

$R_1 = CH_3, CH_2CH=CH_2, (CH_2)_nC_6H_5$ n=1–4;

$R_2 = CH_3, C_2H_5, CH_3(CH_2)_3, (CH_3)_2CH, C_6H_5, C_6H_5CH_2, C_6H_5(CH_2)_2$;

X = pharmacologically acceptable anion.

of which 3β-[4-iodophenyl]-tropan-2β-carboxylic acid methyl ester tartrate is an example have been demonstrated to have a high affinity for binding to cocaine receptors, such as the dopamine transporters and other neurotransmitters of the brain. As the compounds bear an iodine atom, this iodine can be substituted with a radioactive isotope, such as I-125 or I-123. Iodinated compounds of this type have advantages over prior art tritiated or carbon-14 labeled compounds. Notably, the high specific activity, reduced specimen quenching and absorption, and susceptibility for use in SPECT scanning and the like, offers advantages not found in prior art compounds.

3β-(phenyl)tropan-2-carboxylic acid methyl ester is an examplary ligand, and the invention is discussed below in terms of this compound. The compound is nitrated with nitrosonium tetrafluoroborate in acetonitrile, to give a p-nitro derivative. Catalytic hydrogenation of this derivative, using a Raney nickel catalyst, converts the nitro group, to an aminated intermediate. Diazotization, in the presence of methylene iodide, gives the compound of this invention.

Studies showing the high affinity of this compound for dopamine transporters and other cocaine receptors, such as neurotransmitters in the brain, have been conducted, demonstrating the utility of the invention.

DETAILED DESCRIPTION OF THE INVENTION

3β-[4-iodophenyl]-tropan-2β-carboxylic acid methyl ester tartrate is synthesized according to the process outlined in Chart I. Nitration of 3β-(phenyl)tropan-2-carboxylic acid methyl ester (1) with nitrosonium tetrafluoroborate in acetonitrile gives the p-nitro compound 2. Catalytic hydrogenation of 2 using Raney nickel as catalyst afforded the p-amino compound 3. Diazotization of 3 in the presence of methylene iodide followed by treatment with tartaric acid gives the examplary compound of the invention. The parameters of the process steps, per se, are well known, and familiar to those of ordinary skill in the art. These reaction mechanisms, per se, do not constitute an aspect of the invention.

The obtained salt has a melting point of 72°–74° C. It has a high solubility in conventional solvents including water, acid, base, methanol, ethanol and acetone solvents. The compounds of the invention are relatively insoluble in chloroform, ether, petroleum ethers and benzene and not stable with respect to heat or light.

CHART I:

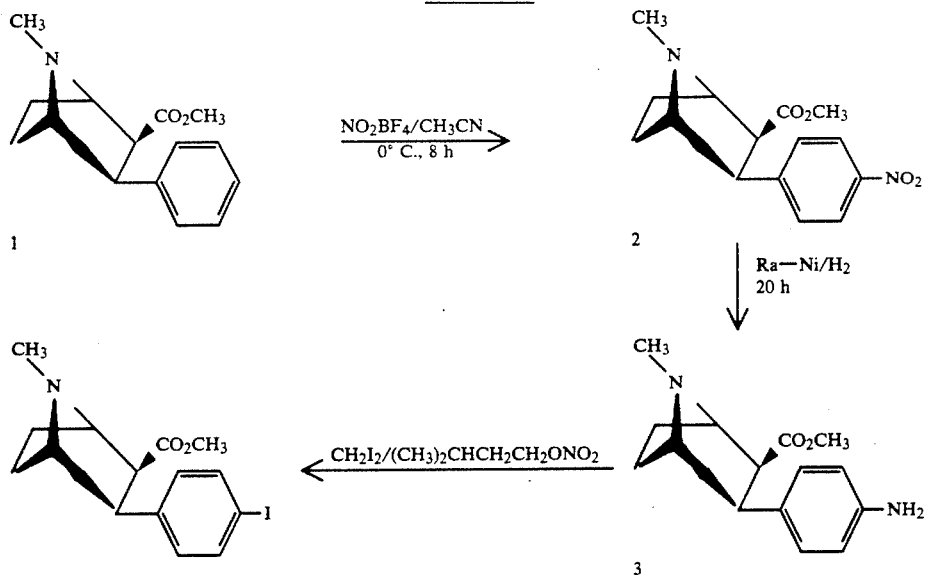

3β-[4-iodophenyl]-tropan-2β-carboxylic acid methyl ester tartrate has been demonstrated to have a high relative affinity for dopamine neurotransmitters. Affinity was determined according to the protocol of Carroll et al, discussed above. Using this protocol, a prior art binding ligand, [$^3$H]WIN 35,428 is co-incubated with various concentrations of the binding ligand to be measured, in 0.5 nM [$^3$H]WIN 35,428 in 10 nM phosphate buffer, pH 7.4, containing 0.32M sucrose. The reaction is allowed to proceed for two hours, at which time the reaction is terminated. The bound radioactivity is measured. The relative affinity for various binding ligands at the dopamine transporter site, determined according to this protocol, is set forth below, in terms of the IC$_{50}$ value obtained.

| DRUG | IC$_{50}$ |
| --- | --- |
| Cocaine | 89.00 nM |
| WIN 35,065-2 | 25.00 nM |
| GBR 12,909 | 22.00 nM |
| WIN 35,428 | 14.00 nM |
| 3β-[4-iodophenyl]-tropan-2β-carboxylic acid methyl ester tartrate | 1.25 nM |

On the basis of the above affinities, it is clear that use of radioactive isotopes of iodine in the synthesis route described above will provide a radiodetectable compound, bound to neurotransmitters in the brain. Various imaging techniques exist to determine the placement, number and relative details of the neurotransmitters bound to. SPECT scanning, as well as more conventional and/or simplified scanning techniques, can be taken advantage of, in giving details as to the number and location of neurotransmitters. Thus, this process may be used, e.g., for the diagnosis of Parkinson's disease, based on the dopamine transmitters bound to upon IV administration of the compound of this invention.

A brief description of an imaging procedure is as follows: Tracer quantities of the radioactive iodine labeled ligand will be injected intravenously into subjects positioned in a SPECT scanner. After injection of the compound, the scanner will be turned on to begin to collect data. The ligand will preferentially localize to dopamine transporters over about one hour, with the best localization perhaps occurring at about 30–50 minutes. The amount of compound bound will reflect the density of transporters. The target of these experiments will be the basal ganglia where the dopamine transporters are concentrated. Disease states such as Parkinson's disease will show a reduction in transporter density.

Obviously, modifications and variations of the present invention are possible in light of the above teachings. In particular, various synthesis parameters, as well as scanning methodologies and the like may be employed, as alternatives to the exemplification set forth. It is therefore to be understood that within the scope of the appended claims, the invention may be practiced otherwise than as specifically described herein.

What is claimed is:
1. A compound of the formula below,
Where the broken line represents an optional chemical bond and the substituents at 2 and 3 may be at any position;
the iodo substituent may be at o, m, p, or multisubstituted;
R$_1$=CH$_3$, CH$_2$CH=CH$_2$, (CH$_2$)$_n$C$_6$H$_5$ n=1–4;
R$_2$=CH$_3$, C$_2$H$_5$, CH$_3$(CH$_2$)$_3$, (CH$_3$)$_2$CH, C$_6$H$_5$, C$_6$H$_5$CH$_2$, C$_6$H$_5$(CH$_2$)$_2$;
X=pharmacologically acceptable anion

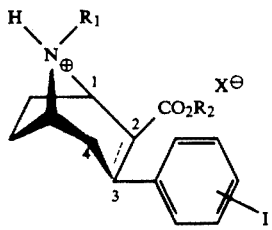

wherein said iodo substituent is radioactive.
2. The compound of claim 1, wherein said isotope is $^{123}$I.
3. The compound of claim 1, wherein said isotope is $^{125}$I.

4. A method of assaying for the presence, of neurotransmitters in the brain of a mammal, comprising administering an effective amount of the compound of claim 1 bearing a radioactive iodine isotope in a pharmaceutically acceptable carrier to said mammal, allowing said radioactively labeled compound to bind to neurotransmitters in the brain of said mammal, and scanning the brain of said mammal to determine the presence of radioactive iodine bound thereto, wherein the presence of radioactive iodine corresponds to a neurotransmitter site.

5. The process of claim 4, wherein said neurotransmitter is a dopamine transmitter.

6. The process of claim 4, wherein said radioactive iodine isotope is $^{125}I$ or $^{123}I$.

* * * * *

UNITED STATES PATENT AND TRADEMARK OFFICE
CERTIFICATE OF CORRECTION

PATENT NO. : 5,128,118
DATED : JULY 7, 1992
INVENTOR(S) : FRANK I. CARROLL, ET AL

It is certified that error appears in the above-identified patent and that said Letters Patent is hereby corrected as shown below:

Column 1, line 51, change "Parkinson'" to --Parkinson's--;
       line 57, after "affinity", insert --and--.

Column 2, line 20, change "X=pharmacologically" to
    --X⁻=pharmacologically--.

Column 3, lines 36-37, after "measured", insert --.--.

Column 4, line 52, change "X-pharmacologically" to
    --X⁻-pharmacologically--.

Column 6, Claim 5, line 5, change "transmitter" to
    --transporter--.

Signed and Sealed this

Twenty-second Day of March, 1994

*Attest:*

BRUCE LEHMAN

*Attesting Officer*    *Commissioner of Patents and Trademarks*